Figure 1:
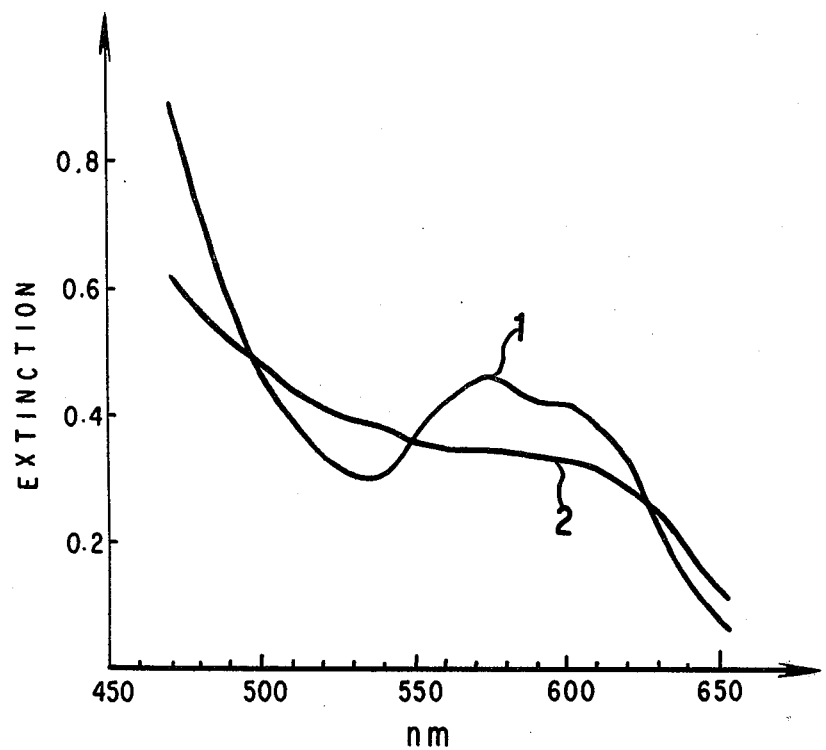

United States Patent [19]

Zander et al.

[11] 4,341,527

[45] Jul. 27, 1982

[54] PROCESS AND REAGENT FOR DETERMINATION OF THE HEMOGLOBIN CONTENT OF BLOOD

[76] Inventors: Rolf Zander, Reinhold-Schneider-Str. 1; Werner Lang, Alter Ruh-Weg, both of Mainz; Hans U. Wolf, Lisztstrasse 10, Neu-Ulm, all of Fed. Rep. of Germany

[21] Appl. No.: 170,575

[22] Filed: Jul. 21, 1980

Related U.S. Application Data

[63] Continuation of Ser. No. 5,456, Jan. 22, 1979, abandoned.

[30] Foreign Application Priority Data

Jan. 25, 1978 [DE] Fed. Rep. of Germany ....... 2803109

[51] Int. Cl.$^3$ ............................................. G01N 33/72
[52] U.S. Cl. ..................................... 23/230 B; 23/913; 252/174.21; 252/408; 356/40
[58] Field of Search .............. 23/230 B, 913; 252/408, 252/174.21

[56] References Cited

U.S. PATENT DOCUMENTS

| | | | |
|---|---|---|---|
| 3,816,262 | 6/1974 | Monte | 23/230 B X |
| 3,847,545 | 11/1974 | Shanbrom | 23/230 B |
| 3,964,865 | 6/1976 | Das | 23/230 B |
| 4,011,045 | 3/1977 | Bonderman | 23/230 B |
| 4,290,772 | 9/1981 | Frey | 356/40 X |
| 4,297,238 | 10/1981 | Vormbrock | 23/913 |

*Primary Examiner*—Sidney Marantz
*Attorney, Agent, or Firm*—Hammond & Littell, Weissenberger & Muserlian

[57] ABSTRACT

A reagent for photometric determination of the hemoglobin content of blood, which produces a characteristic color upon addition of the blood sample, consisting of an aqueous alkaline solution comprising a water-soluble, non-ionic detergent, whereby all hemoglobin-derivatives occurring in the blood and hemederivatives are converted into a unitary end product having a distinct absorption maximum in the visible spectral range.

6 Claims, 1 Drawing Figure

PROCESS AND REAGENT FOR DETERMINATION OF THE HEMOGLOBIN CONTENT OF BLOOD

This is a continuation of copending application Ser. No. 06/005,456, filed Jan. 22, 1979, now abandoned.

This invention relates to a novel process and reagent for photometric determination of the hemoglobin content of blood, which produce a characteristic color upon addition of the blood sample.

BACKGROUND OF THE INVENTION

The quantitative determination of hemoglobin in blood is one of the most frequently performed analyses in clinical chemistry. For this purpose various methods have been developed in the course of this century, which differ considerably from each other with respect to accuracy, reliability and reproducibility [cf. L. Hallmann, *Klinische Chemie und Mikroskopie* (10th ed.), Thieme-Verlag, Stuttgart, Germany (1966); R. J. Henry, *Clinical Chemistry* (1st ed.), Harper and Row, New York (1964); R. Richterich, *Klinische Chemie* (3rd ed.), Karger, Basel, Switzerland (1971); R. J. Henry et al.; *Clinical Chemistry* (2nd ed.), Harper and Row, New York (1974); and W. Rick, *Klinische Chemie und Mikroskopie* (4th ed.), Springer Verlag, Berlin/Heidelberg/New York (1976)], namely:

1. Spectrophotometric methods (as carboxy-hemoglobin, oxy-hemoglobin or cyano-hemiglobin (cyanomethemoglobin), as cyano-hematin, acid or alkaline hematin, as well as pyridine-hemochromogen);
2. Gasometric methods (determination of oxygen- or carbonmonoxide capacity);
3. Chemical methods (determination of iron content);
4. Other methods (refractometry, density measuring enzymatic reactions such as the pseudoperoxidase activity of the hemoglobin).

Among these, the spectrophotometric cyano-hemiglobin method has been universally accepted and is now being used worldwide. During the period from 1953 to 1963, after practically all of the laboratories had introduced this method in place of others [cf. J. Spaander, Die Verwertung von Blutuntersuchungen, Strahlenschutz in Forschung und Praxis 4, 122–127 (1964), and F. W. Sunderman, Status of Clinical Hemoglobinometry in the United States, Am. J. Clin. Pathol. 43, 9–15 (1965)] and a cyano-hemiglobin standard was recommended [R. K. Cannan, Proposal for a Certified Standard for Use in Hemoglobinometry—Second and Final Report, J. Lab. Clin. Med. 52, 471–476 (1958)], it was recommended for universal adoption [see Ärztl. Labor. 8, 188 (1962); and Brit. J. Haemat. 13, 71–75 (1967)]. Since that time this method is recognized as the routine method.

In Germany it has acquired the function of a reference method, that is, other methods are allowed to be applied only if the relationship of the results obtained therewith to the result of the reference method is known [see German Norms: Determination of the hemoglobin content of blood; DIN Vornorm 58 931 (1970)].

The introduction of the cyano-hemiglobin method as a standard has engendered a certain bias against other methods among those skilled in the art: "Hemiglobincyanide is the only known stable hemoglobin-derivative" (R. Richterich, supra); "all other methods . . . are to be rejected" (W. Rick, supra); " . . . cyano-hemiglobin (most exact proof)" (L. Hallmann, supra).

The principle of the cyano-hemiglobin method consists of oxidizing the hemoglobin with potassium ferricyanide to hemiglobin and converting same with potassium cyanide to cyano-hemiglobin, using a modified so-called Drabkin's solution as the reaction solution, as indicated originally by van Kampen and Zijlstra [E. J. van Kampen and W. G. Zijlstra, Standardization of Hemoglobinometry, II; The Hemoglobincyanide Method. Clin. Chim. Acta 6, 538–544 (1961); and W. G. Zijlstra and E. J. van Kampen, Standardization of Hemoglobinometry, I. The Extinction Coefficient of Hemoglobincyanide at $\eta = 540$ mµ; $\epsilon_{HiCN}^{540}$, Clin. Chim. Acta 5, 719–726 (1960)]. This method has the following advantages:

1. Use of only one reaction solution;
2. All hemoglobin derivatives of the blood are included (desoxy-hemoglobin, oxy-hemoglobin, carboxy-hemoglobin, hemiglobin and substantially all sulf-hemoglobin as well);
3. Cyano-hemiglobin possesses a broad and flat extinction maximum at 540 nm, so that reliable results may be obtained even with unsophisticated filterphotometers.
4. The Lambert-Beer law is valid over a wide measuring range;
5. Production and shipment of stable standard solutions for control purposes is possible; they may be produced from crystalline hemoglobin as well as from washed erythrocytes;
6. Cyano-hemiglobin is a stable hemoglobin derivative, so that the measurement of the extinction can be effected after several minutes as well as several days later.

The disadvantages of the cyano-hemiglobin method are the following [R. J. Henry, *Clinical Chemistry* (1st ed.), page 740, Harper and Row, New York (1964)]:

1. The toxicity of the reaction solution requires special handling measures (use of mechanical pipettes, careful discarding of the solution in the sink);
2. The reaction solution does not remain stable over a long time; it is sensitive to light and must be stored correspondingly (brown flasks or the like);
3. The concentrations of the reactants have to be maintained exactly; this is especially applicable to the buffer, which has to guarantee a definite pH-value;
4. The various hemoglobin derivatives have different reaction periods, some of which are entirely too long. Originally, a reaction period of 3 minutes was indicated for all hemoglobin derivatives (E. J. van Kampen and W. G. Zijlstra, supra), but this statement had to be modified subsequently.

In 1965, J. B. Taylor and J. D. M. Miller [A source of error in the cyanmethemoglobin method of determination of hemoglobin concentration in blood containing carbon monoxide, Am. J. Clin. Pathol. 43, 265–271 (1965)] showed that the cyano-hemiglobin formation in the presence of carboxy-hemoglobin is distinctly prolonged and, therefore, considerable errors in the determination of hemoglobin must occur.

In 1965 E. J. van Kampen and W. G. Zijlstra [*Advances in Clinical Chemistry*, Vol. 8, page 160 (H. Sobotka and C. P. Stewart, editors), Academic Press, New York 1965] suggested a reaction time of 90 minutes in those instances where the blood to be tested is expected to contain carboxy-hemoglobin.

In 1967, F. L. Rodkey [Kinetic aspects of cyanmethemoglobin formation from carboxyhemoglobin, Clin. Chem. 13, 2–5 (1967)] showed that the conversion of HbCO into cyano-hemiglobin at room temperature takes 90 to 120 minutes, while $HbO_2$ takes only 10 minutes. This author is able to shorten the reaction period for conversion of HbCO into cyano-hemiglobin to 15 minutes, if the concentration of potassium ferricyanide is increased five-fold. In 1967, E. W. Rice [Rapid determination of total hemoglobin as hemoglobin cyanide in blood containing carboxyhemoglobin, Clin. Chim. Acta 18, 89–91 (1967)] solved the problem by heating the solution to 56° C. Then the reaction of HbCO to cyano-hemiglobin is complete after 3 to 5 minutes.

The fact that carboxy-hemoglobin oxidizes to hemiglobin much slower than other derivatives (Hb, $HbO_2$), is utilized in the so-called Hoppe-Seyler test for a qualitative HbCO-proof in blood [cf. W. Massmann, Deutsche Med. Wochenschrift 79, 1140–1142 (1940)].

Further possibilities of error could be excluded. For example, a precipitation of plasma-proteins and a turbidity connected therewith could be avoided [cf. P. Green and C. F. J. Teal, Am. J. Clin. Pathol. 32, 216–217 (1959)] by adding a detergent to the reaction solution [E. J. van Kampen and W. G. Zijlstra, 1961, supra].

OBJECTS OF THE INVENTION

It is an object of the present invention to provide a reagent and a reliable method for determining the hemoglobin content of blood, which has the advantages of the present cyanmethemoglobin method but is free of its disadvantages.

Other objects and advantages of the present invention will become apparent as the description thereof proceeds.

DESCRIPTION OF THE INVENTION

The object is achieved in accordance with the instant invention by providing a reagent consisting of an aqueous, alkaline solution comprising a water-soluble, non-ionic detergent, whereby all hemoglobin derivatives present in blood and heme derivatives are converted into a uniform final product with a pronounced absorption maximum in the visible spectral range. In particular, those detergents which lead to a final product with an absorption maximum at about 575 nm. are preferred.

More particularly, the reagent pursuant to the present invention consists of an aqueous 0.05–0.5 M solution of sodium hydroxide or potassium hydroxide comprising 0.5–10% by weight of detergent.

The detergent may be a polyethyleneglycol p-alkyl-phenyl ether of the formula

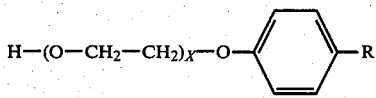

wherein

R is alkyl of 1 to about 12 carbon atoms, such as methyl, ethyl, propyl, butyl, pentyl, hexyl, heptyl, octyl, nonyl, decyl, undecyl or dodecyl, and X is an integer from 7 to 12, inclusive, or a polyethyleneglycol lauryl, cetyl, oleyl or stearyl ether. The preferred embodiment of the detergent is decaethyleneglycol p-tert. octyl-phenyl ether.

The determination of hemoglobin as alkaline hematin was described for the first time by H. Wu, J. Biochem. 2, 173–180 (1922). However, that method distinguished itself by a certain awkwardness; upon addition of concentrated hydrochloric acid, hemoglobin was converted into hematin, which was subsequently alkalized with sodium hydroxide solution. Therefore, the time required for a determination was also about 1 hour. In comparison to other methods, such as acid hematin, methemoglobin or cyano-hemiglobin, Wu recognized the advantage that disturbances by other plasma components did not occur. J. W. Clegg and E. J. King, Brit. Med. J. 2, 329–333 (1942) disclosed a method for determination of hemoglobin via alkaline hematin, for which 0.1 N sodium hydroxide was used as the reaction solution; after addition of the blood, it was heated on a water bath at 100° C. for 4–5 minutes. The authors considered this procedure to be necessary because fetal hemoglobin and alkali-resistant hemoglobin of adults showed too slow a color development.

After 1942, there were a number of authors who reported satisfactory results with the alkaline hematin method [E. J. King et al., Lancet 2, 563–566 (1948); R. G. MacFarlane et al., Lancet 2, 282–286 (1948); R. Donaldson et al., Lancet 1, 874–881 (1951); E. J. King et al., Lancet 1, 1044–1045 (1951); and J. F. Scaife, Analyst 80, 562–565 (1955)]. Several modifications were also suggested; for example, the use of another wave-length (J. F. Scaife, supra) or of a special standard [King et al.; Brit. Med. J. 2, 349–350 (1947)].

On the other hand, other authors rejected the alkaline hematin method because of excessively long reaction periods or disturbing effects of plasma components [E. Ponder, J. Biol. Chem. 144, 339–342 (1942); and F. W. Sunderman et al.; American J. Clin. Pathol. 23, 519–598 (1953)]. The cyano-hemiglobin method widely used at the same time displaced the alkaline hematin method more and more, so that later on "a discussion of alkaline hematin could be obviated" [S. Legowski et al; Deutsche Med. Wochenschr. 87, 1953–1960 (1962)].

Compared to the classic method based on alkaline hematin, the process according to the present invention differs in that an alkaline hematin with special properties regarding spectrum, rate of formation and durability is formed, which is hereinafter referred to as "alkaline hematin D-575".

The following characteristics and advantages are connected with the present invention:

1. All heme derivatives and hemoglobin derivatives are converted quantitatively into a uniform reaction product, i.e. alkaline hematin D-575, and embraced by the photometric measurement: hemoglobin, oxy-hemoglobin, carboxy-hemoglobin, hemiglobin, sulf-hemiglobin, cyano-hemiglobin, fetal hemoglobin as well as chlorohemin.

2. Formation of the alkaline hematin D-575 after addition of the blood sample to the reaction solution is concluded after 2 minutes at the latest, and the reaction product will show for weeks the same extinction. This is valid without exception for all heme and hemoglobin derivatives mentioned under 1.

3. The reaction solution which is used has ideal properties:

a. Only one reaction solution is required.

b. The reaction solution is indefinitely stable.

c. Handling of the reaction solution is virtually harmless.

d. The reaction solution may be stored in conventional glass or plastic containers at room temperature.

e. The reaction solution is insensitive to light.

f. The reaction solution is producible in a simple way and it is cheap.

g. The chemicals used for the reaction solution are exchangeable, that is, different chemicals may be used with the same success. NaOH or also KOH may be used; the detergent may be, for example: polyethyleneglycol p-tert. octylphenyl ether (especially polyethyleneglycol-mono-[p-(1,1,3,3,-tetramethylbutyl)-phenyl]-ether, available under the trade name Triton X-100), polyethyleneglycol lauryl ether, polyethyleneglycol cetyl ether, polyethyleneglycol oleyl ether and polyethyleneglycol stearyl ether.

h. The concentration of the reactants, NaOH and detergent, is not critical, that is, a considerable deviation from the optimal conditions has practically no influence on the practicability of the process. If the NaOH is changed in a range of concentration from 0.05 to 0.5 M and that of the detergent in the range from 1 to 4%, the spectral behavior of the reaction product does not change, merely the reaction period required for the determination is extended from 1 to 2 minutes to 5–10 minutes.

i. The pH-value (see above NaOH-concentration) and the temperature have no effect within a wide range on the practicability of the process.

j. Contrary to the diluted blood, the reaction product, alkaline hematin D-575, has an intense green color (color impression at a light path from 1 to 2 cms). The result is that the end of reaction can be judged with the eye, at least coarsely.

k. The alkaline medium of the reaction solution is especially suitable for proof of hemoglobin [cf. R. Barer et al; Clin. Chim. Acta 2, 140–156 (1957)]; the erythrocytes are completely hemolyzed, the erythrocyte membranes are dissolved and liberate the hemoglobin adsorbed on them; finally, a precipitation of the plasma proteins (turbidity) is impeded.

4. The reaction product, alkaline hematin D-575, exhibits ideal properties:

a. The extinction is large enough for performing a hemoglobin determination with only 10 to 30 microliters of blood (using conventional quantities of reaction solution, namely 2 to 5 ml).

b. The Lambert-Beer Law is valid over a wide range;

c. The spectrum of the reaction product shows a broad maximum at a wave-length of 575 nm (therefore, the designation "alkaline hematin D-575"), so that, even with unsophisticated filterphotometers, reliable determinations may be carried out. In the abovementioned range, the spectrum is independent of the concentration of the reactants; it differs clearly from alkaline hematin without addition of a detergent. The spectral behavior of alkaline hematin D-575 (curve 1) in comparison to the spectrum of alkaline hematin (curve 2), is shown in the attached drawing, FIG. 1. The spectra were obtained by diluting a cyanohemiglobin standard solution (212.4 mg/100 ml) with the same volume of 0.1 M NaOH (formation of alkaline hematin) or 0.1 M NaOH with 2.5% of decaethyleneglycol p-tert. octylphenyl ether added (formation of alkaline hematin D-575), respectively. This composition gives optimal results as far as the reaction period is concerned. While alkaline hematin in NaOH exhibits a spectrum with a plateau between 500 and 600 nm often described in the literature [cf. for example, F. T. Hunter, *The Quantitation of Mixtures of Hemoglobin Derivatives by Photoelectric Spectrophotometry*, Thomas, Springfield (1951)], alkaline hematin D-575 has a broad maximum at 575 nm in the presence of a non-ionic detergent. This effect is not obtained with ionic detergents. While anionic detergents, such as sodium dodecyl sulfate, do not produce the characteristic band at 575 nm, cationic detergents, such as benzyl-diisobutyl-phenoxyethoxy-dimethyl-ammonium chloride or dodecyl-dioxy-ethyl-benzylammonium chloride lead to a brown precipitation when blood is added. The effect of the non-ionic detergent must be due to a non-specific influence, because it is independent of its structure [with reference to the alteration of the hemoglobin spectrum by inert solvents, cf. L. Heilmeier, *Medizinische Spektrophotometrie*, page 116, Fischer, Jena (1933)].

5. Since alkaline hematin D-575 is very stable, standard solutions thereof may be prepared with known concentrations from washed erythrocytes, from crystalline hemoglobin and from crystalline chloro-hemin. The latter method, in particular, is highly recommended for the production of a standard, because chloro-hemin is a simple, well-defined substance (mol. wt. 651.97, empirical formula $C_{34}H_{32}Cl\ Fe\ N_4O_4$), very readily soluble in the described reaction solution and shows clearly the typical spectral properties of alkaline hematin D-575, that is, it is quantitatively converted into alkaline hematin D-575.

It may be considered as a special advantage that the cyano-hemiglobin standard solutions in use worldwide can be used as well after dilution with the reaction solution (FIG. 1). This means that a standardization of the novel method may be achieved with already existing standards.

The following example illustrates the invention: A volume of 20 microliters of blood is transferred by means of a calibrated capillary or a so-called Sahli-pipette into a graduated container containing 3 ml of reaction liquid. The graduated container consists, for example, of clear polystyrol and has an edge length of 1 cm. At its upper end is a plastic closure which is normally sealed and is only opened immediately before the measuring procedure. The reaction solution in the graduated container remains stable for months so that filled such containers may be stored over a corresponding period of time.

The reaction solution consists, for example, of aqueous 0.1 M NaOH to which 2.5% by weight of decaethyleneglycol p-tert. octylphenyl ether has been added. This detergent has proved to be especially suitable, because it is available in liquid form and can be easily handled. After having added the blood sample, the blood is admixed with the reaction solution by shaking the graduated container, whereupon the conversion of all hemoglobin derivatives begins immediately. The solution assumes right away an intensely green color. Measuring the extinction in the photometer at a wave-length of 575 nm may be effected after 1 minute or at the latest 2 minutes. Since the extinction will remain stable for days, measuring may be done later as well. As photometers may be used commercial filterphotometers, where a filter is chosen which allows a narrow range to pass at 575 nm. A suitable filter photometer is described, for example, in German Auslegeschrift No. 2,448,206.

When blood of a normal hemoglobin concentration of about 16 g/100 ml is used, there results from this ratio of dilution an extinction of about 0.46 at the mentioned wave-length, measured in comparison to a graduated container of the same length (1 cm) filled with water.

The comparison with a standard solution (for example a 0.1 mM chloro-hemin solution in the same reaction solution or a cyano-hemiglobin solution of a known concentration, diluted with the same volume of reaction solution) yields the desired hemoglobin concentration in g/100 ml.

While the present invention has been illustrated with the aid of a certain specific embodiment thereof, it will be readily apparent to others skilled in the art that the invention is not limited to this particular embodiment, and that various changes and modifications may be made without departing from the spirit of the invention or the scope of the appended claims.

We claim:

1. A reagent for the photometric determination of the hemoglobin content of blood, which, upon addition to a blood sample, produces a characteristic color, said reagent consisting of an aqueous 0.05–0.5 M solution of sodium hydroxide or potassium hydroxide comprising 0.5–10% by weight of a water-soluble, liquid, nitrogen-free, nonionic detergent selected from the group consisting of
   (a) a polyethyleneglycol p-alkylphenyl ether of the formula

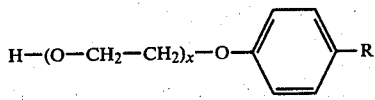

wherein
   x is an integer from 7 to 12, inclusive, and
   R is an alkyl of 1 to 12 carbon atoms;
   (b) a polyethyleneglycol lauryl ether;
   (c) a polyethyleneglycol cetyl ether;
   (d) a polyethyleneglycol oleyl ether; and
   (e) a polyethyleneglycol stearyl ether,
whereby all hemoglobin derivatives occurring in blood and heme derivatives are converted into a uniform end product having a distinct absorption maximum in the visible spectral range.

2. A reagent of claim 1, which produces on addition to blood an end product having an absorption maximum at about 575 nm.

3. A reagent of claim 1, where said detergent (a) is decaethyleneglycol p-tert.octylphenyl ether.

4. In the method of determining the hemoglobin content of blood by hemolyzing the blood, converting the hemoglobins into hematin with an aqueous alkaline solution and photometrically determining the alkaline hematin content, the improvement wherein the conversion of the hemoglobins into hematin is effected with an aqueous 0.05–0.5 M solution of sodium hydroxide or potassium hydroxide comprising 0.5–10% by weight of a water-soluble, liquid, nitrogen-free, non-ionic detergent selected from the group consisting of
   (a) a polyethyleneglycol p-alkylphenyl ether of the formula

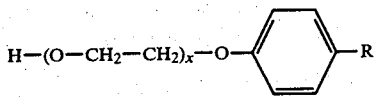

wherein
   x is an integer from 7 to 12, inclusive, and
   R is an alkyl of 1 to 12 carbon atoms;
   (b) a polyethyleneglycol lauryl ether;
   (c) a polyethyleneglycol cetyl ether;
   (d) a polyethyleneglycol oleyl ether; and
   (e) a polyethyleneglycol stearyl ether,
whereby all hemoglobin derivatives which occur in blood and heme derivatives are converted into a uniform product having a distinct absorption maximum in the visible spectral range in which the subsequent photometric measurement is carried out.

5. The method of claim 4, where said uniform product has an absorption maximum at a wavelength of about 575 nm.

6. The method of claim 4, where said detergent (a) is decaethyleneglycol p-tert.octylphenyl ether.

* * * * *